United States Patent [19]

Blau

[11] Patent Number: 4,808,820
[45] Date of Patent: Feb. 28, 1989

[54] ELECTRON-EMISSION FILAMENT CUTOFF FOR GAS CHROMATOGRAPHY + MASS SPECTROMETRY SYSTEMS

[75] Inventor: David A. Blau, Los Altos, Calif.
[73] Assignee: Hewlett-Packard Company, Palo Alto, Calif.
[21] Appl. No.: 99,935
[22] Filed: Sep. 23, 1987
[51] Int. Cl.⁴ .............................................. B01D 59/44
[52] U.S. Cl. .................................... 250/281; 250/282; 250/423 R; 250/427; 250/288
[58] Field of Search ................... 250/423 R, 427, 281, 250/282, 283, 288 A; 324/459

[56] References Cited

U.S. PATENT DOCUMENTS

| | | | |
|---|---|---|---|
| 3,866,041 | 2/1975 | Attic | 250/281 |
| 3,937,955 | 2/1976 | Comisarow et al. | 250/283 |
| 4,075,475 | 2/1978 | Risby et al. | 250/282 |
| 4,636,680 | 1/1987 | Bills | 313/264 |
| 4,714,891 | 2/1987 | Morrison | 324/459 |
| 4,721,858 | 1/1988 | Buchanan | 250/382 |
| 4,730,111 | 3/1988 | Vestel et al. | 250/288 |

Primary Examiner—Bruce C. Anderson

[57] ABSTRACT

A gas chromatography plus mass spectrometer (GC/MS) system includes a gas chromatograph, a mass spectrometer, and a computer interface to both of them. The mass spectrometer includes an ion source with an electron emission filament which can be damaged if on during the time a solvent peak is eluting from the chromatography. The filament is regulated to provide a constant emission rate by feedback which causes a current source to compensate deviations from a desired emission level. When a solvent peak begins to elute, the concomitant sudden cooling of the filament is sensitively reflected in the feedback to the current source. a comparator AC-coupled to the current source input can be used in shutting off the current source when the emission current abruptly drops. A computer controller can reactivate the filament in response to a decrease in ambient pressure or elapse of a predetermined duration so that component peaks following the solvent peak can be analyzed.

16 Claims, 2 Drawing Sheets

ELECTRON-EMISSION FILAMENT CUTOFF FOR GAS CHROMATOGRAPHY + MASS SPECTROMETRY SYSTEMS

BACKGROUND OF THE INVENTION

The present invention relates to mass spectrometry, and, more particularly, to mass spectrometers used with gas chromatographs. A major objective of the present invention is to avoid ion source contamination and ion source filament burnout due to ionization of a solvent peak eluting from a gas chromatograph.

The gas chromatograph and the mass spectrometer combine synergistically to provide an instrument, herein referred to as the GC/MS system, of considerable importance in the field of analytical chemistry. A gas chromatograph separates the components of a mixture in solution by volatizing the components of the solution into a carrier gas stream which is passing over a liquid stationary phase. This process takes place in a packed or capillary chromatography column.

A volatized component must be ionized before it can be analyzed by the mass spectrometer. Accordingly, the eluting components are introduced into an ionization chamber of an ion source. Electron impact (EI) ionization is the most common approach to ionization, and is the approach addressed by the present invention.

In EI ionization, a large current is used to heat a filament so electrons are emitted from its surface. The emitted electrons are accelerated toward the ionization chamber by an electric field, with additional directivity being supplied by a reflector and a magnet. The emitted electrons enter the ionization chamber and collide with eluting molecules, which are thus ionized. The ionized molecules are drawn into the analyzer section of the mass spectrometer by the electric field of a "drawout lens". The analyzer section includes a filter which separates ionized molecules according to their mass-to-charge rations.

Mass spectrometers require low operating pressures, and according employ regulated multistage vacuum pump systems which are monitored by high and low vacuum gauges. These pumping systems are capable of maintaining the low pressures required by the mass spectrometer while the effluent from a column is introduced into the mass spectrometer.

A problem can occur in GC/MS systems if a large amount of sample is introduced into the ionization chamber while the filament is on. Generally, the solvent introduced with the sample is much more plentiful than any of the sample components. The elution of the solvent peak from the column can increase the pressure in the ionization chamber significantly. If the filament is on, a surfeit of ionized molecules contaminate the surrounding ion source components and can burn out the filament. Accordingly, it is generally necessary to turn off the ion source filament while a very large peak, such as a solvent peak, is eluting from a column. It is also possible to divert the effluent during solvent elution, but the dead volumes caused by the additional plumbing adversely affect component separation, particularly where capillary columns are used.

There are two classes of approaches to determining when to have the filament off: those based on prediction and those based on detection. Those based on prediction work best when it is known when and how long the solvent peak is going to elute, and when it is known that no peaks of interest will elute before the solvent. In these cases, the filament is left off until a predetermined time has elapsed, during which time the solvent but no peak of interest should have eluted. The filament is then turned on in time to ionize the effluent containing the sample peaks.

This prediction approach is not generally satisfactory. The number of parameters than can be varied during and between chromatographic runs make it difficult to predict solvent peak timing with precision. In addition, there are solvent-mixture systems in which components of interest elute both before and after a solvent peak. Furthermore, it would be desirable to turn off the filament any time a potentially damaging peak arrived at the ionization chamber, whether or not the peak represented the nominal solvent, a component of interest, column bleed, septum or other artifact.

Accordingly, it would be preferable to be able to detect the onset of a solvent or other large peak, and use this detection as a basis for determining when to shut off the filament. For example, the vacuum system of the mass spectrometer generally includes shut-off circuitry associated with its high vacuum gauge. However, the high vacuum gauge is generally too far downstream of the ion source to shut the filament off in time to prevent contamination and potential filament burn-out.

Another approach considered is to use a collector or draw plate current to detect a solvent peak. A collector in the form of an electrode with a positive potential relative to the ionization chamber is often placed just outside the ionization chamber opposite the filament to sweep negative charge out of the chamber. Otherwise, negative charge could accumulate in the chamber and impede emission of electrons from the filament. Elution of a large peak could prevent most electrons from traversing the chamber to reach the collector. A drop in collector current would then be an indication of a solvent peak.

However, the relation between collector current and chamber pressure is complex. For example, the electrons releases by the solvent molecules during ionization can offset the loss of emitted electrons due to ionization. Thus, the drop in collector current is not a sufficiently fast and sensitive indicator of solvent peaks. Similar difficulties confront the use of the draw plate current as a solvent peak indicator.

Heretofore, it has not been practical to detect a solvent peak fast enough to protect the ion source components from contamination and the filament from burn out. Thus, peaks of interest are missed while a filament is off, and damage to the ion source and filament, and loss of a sample run occur as a solvent peak is ionized. What is needed is a reliable method of detecting a solvent peak in time to prevent its ionization.

SUMMARY OF THE INVENTION

When a solvent peak elutes from a gas chromatograph, the pressure at the filament rises. If the filament is on, this pressure will act to cool the filament. Since electron emission is very sensitively related to filament temperature, this cooling can be detected as a function of the change in the electron current. When such cooling is detected, the filament can be switched off to protect the filament from burnout and the ion source and the rest of the mass spectrometer from contamination.

The current through the filament includes two components, a supply current component and an emission current component due to the emission of electrons.

These two components can be separated by using a floating power supply with a current source for the supply current component. A separate path is provided for the emission current component. The emission current component can be used in a feedback loop to the power supply so that the current source is regulated to provide a constant emission current. A drop in the emission current can then be used, directly or indirectly, to control a shut-off switch to the power supply.

After the filament is shut off, it must be reactivated in order to ionize subsequent component peaks. A controller can reactivate the filament after a fixed duration, or when a subsequent pressure drop is detected, for example, by a low vacuum gauge downstream of the ion source.

The present invention provides for ion source protection with minimal change to existing mass spectrometers. The detection is localized at the component most vulnerable to damage by solvent peaks. The detection is very fast since filament cooling is nearly instantaneous and the cooling is sensitively reflected in the emission current. Further features and advantages are apparent from the description below with reference to the following figures.

DESCRIPTION OF THE PREFERRED EMBODIMENTS

Figure 1:
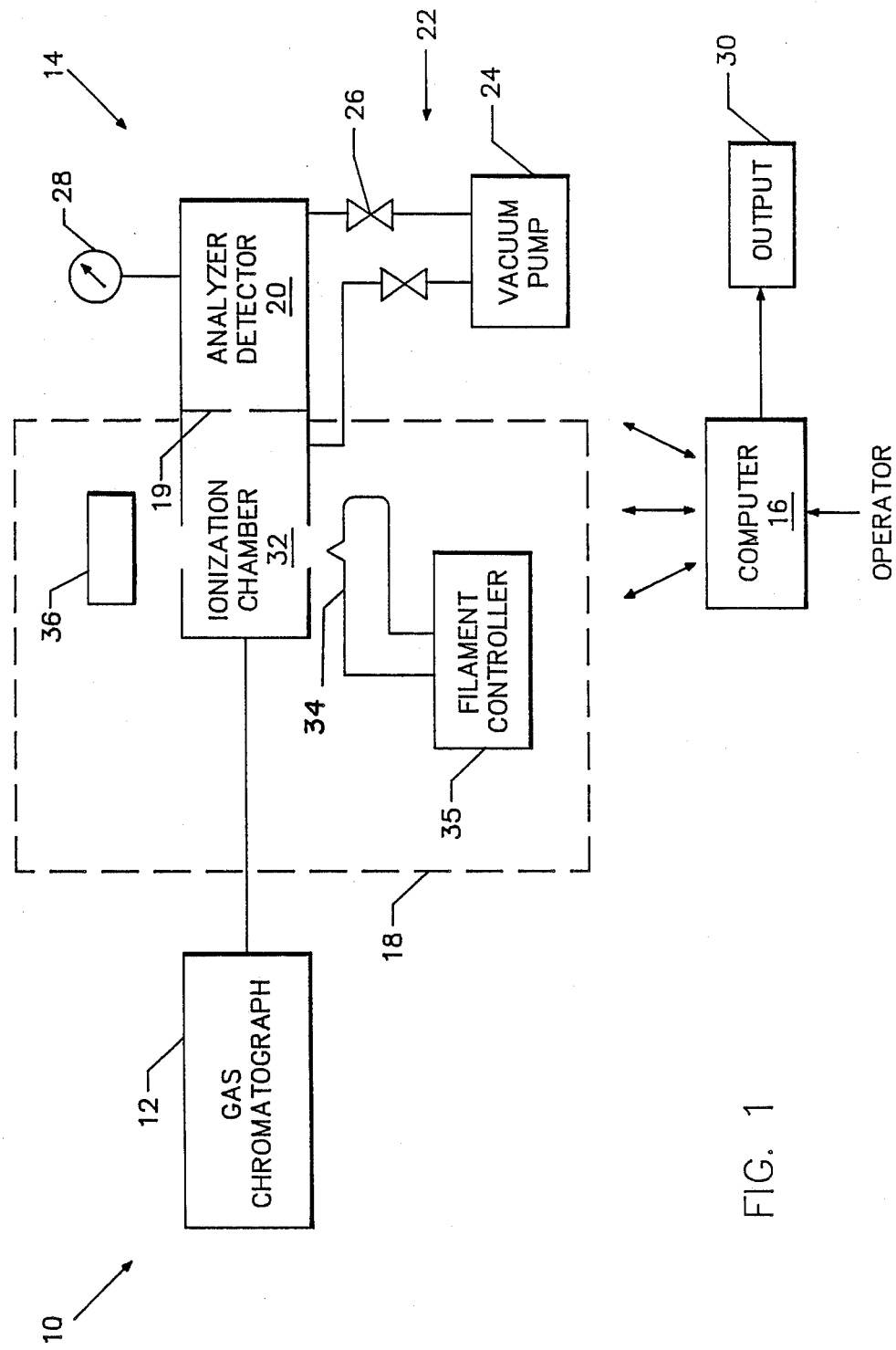
FIG. 1 is a block diagram of a gas chromatography plus mass spectrometry (GC/MS) system in accordance with the present invention.

A GC/MS system 10 includes a gas chromatograph 12 and a mass spectrometer 14 as shown in FIG. 1. A computer 16 provides the interfaces for an operator of the GC/MS system 10 and interface interactively with all illustrated components as schematically indicated by two-way arrows. The mass spectrometer 14 includes an ion source 18, a mass analyzer/detector 20, and a vacuum system 22. A drawing lens 19 is positioned between the ion source 18 and the mass analyzer/detector 20. The vacuum system 22 includes a vacuum pump 24, valves 26 between the pump 24 and respective components of the mass spectrometer 14, and a pressure gauge 28. The illustrated vacuum system components are part of a multistage pumping and monitoring system. An output unit 30 provides for display and storage of data generated by the GC/MS system 10. The ion source 18 includes an ionization chamber 32, a filament 34, a filament control system 35, a collector 36, and means for generating a magnetic field H. These components interact generally as described in the background section above, with the exceptions indicated below.

Figure 2:
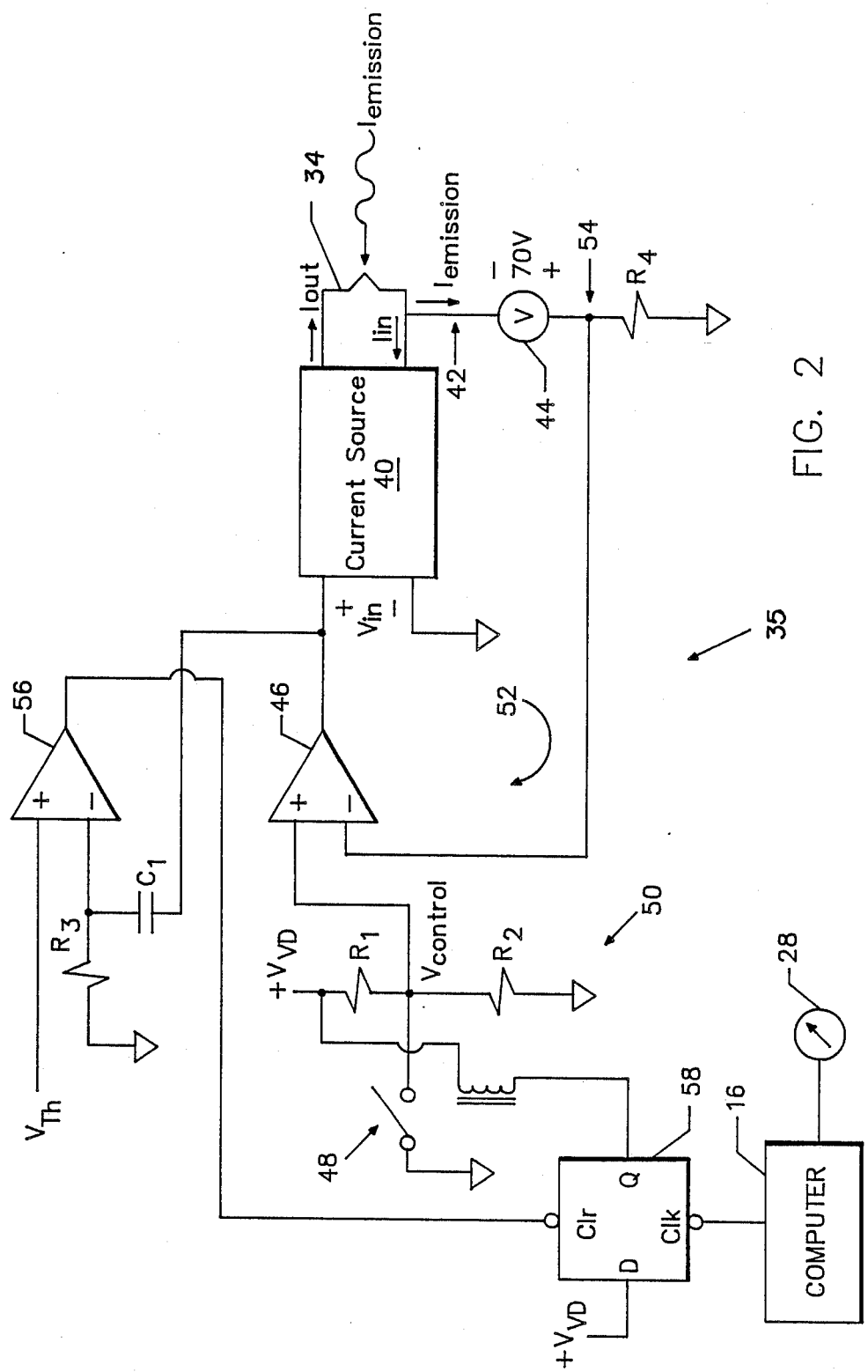
FIG. 2 is a circuit diagram of a control system for a filament of an ion source of the GC/MS system of FIG. 1.

Referring to FIG. 2, the filament control system 35 includes a current source 40 in parallel with the filament 34. This current source 40 is designed so that the supply current $I_{out} = I_{in}$, where $I_{in}$ is the return current. The output of the current source 40 is electrically isolated from ground, i.e., the filament 34 is driven by a floating power supply. An emission current path 42 to ground is provided for emission current associated with the emission of electrons from the filament 34 once it is heated by the supply current. A voltage source 44 on this emission current path 42 is used to maintain a −70 volt potential relative to the ionization chamber 32, FIG. 1, so that emitted electrons are attracted toward the chamber 32.

The current source 40 provides the output current $I_{out}$ as a positive monotonic function of voltage differential at its inputs. The positive input of the current source 40 is fed from a voltage follower 46 in the form of an operational amplifier, its output being determined by the voltage differential at its positive and negative terminals. The negative input of the current source 40 is tied to ground, so the voltage follower 46 alone determines the output of the current source 40.

The status of a relay 48 determines the voltage at the positive terminal of the voltage follower 46. When the relay 48 is open, as illustrated, the voltage at the positive terminal of the voltage follower 46 is fixed by a voltage divider 50. When the relay 48 is closed, the positive terminal is grounded, shutting of the current source 40, and thus the filament 34.

A feedback loop 52 including the voltage follower 46, the current source 40, the filament 34, the emission current path 42, and a feedback line 52 to the negative terminal of the voltage follower 46 regulates the emission of electrons from the filament 34. If the emission current begins to rise from a predetermined steady state level, the voltage at a node 54 on the emission current path 42 rises. This causes the difference between the voltages at the inputs of the voltage follower 46 to diminish. The voltage follower 46 then provides a lower voltage to the current source 40, which then reduces the supply current through the filament 34. The filament 34 cools slightly until the desired steady state emission level is recovered.

Likewise, if the emissions diminish gradually, the voltage at node 54 decreases, and the differential at the voltage follower 46 increases. The output of the voltage follower 46 increases so as to increase the supply current provided by the current source 40. The additional current through the filament 34 heats it until the desired emission level is reestablished.

The output of the voltage follower 46 is capacitively coupled to the negative terminal of a comparator 56 in the form of an operational amplifier. The positive terminal of the comparator 56 is tied to a predetermined threshold voltage, $V_{th}$. The output of the comparator is "high" until the AC component of an increase in voltage follower output exceeds the $V_{th}$.

When an eluting solvent peak enters the ion source 18, the increased pressure at the filament 34 causes it to cool. Since electron emission is proportional to $T^2 e^{-1/t}$, where T is the temperature of the filament 34, the emission current changes dramatically, as does the voltage at the node 54. The feedback loop 52 acts as before, attempting to restore the predetermined emission rate by increasing the voltage output from the voltage follower 46. If the solvent peak is large enough, the increase in voltage follower output triggers the AC-coupled comparator 56 resulting in a negative-going pulse.

The negative-going pulse causes a D-type flip-flop 58 to clear. This flip-flop 58 is arranged with the voltage for the voltage divider 50 at its D input. The GC/MS system computer 16 can set the flip-flop 58 to a high output by sending a negative-going transition to the clock input of the flip-flop 58. Once set, the flip-flop 58 provides the voltage required to set the voltage divider 50 while the filament 34 is active. When the flip-flop 58 is cleared, the relay 48 is closed by the resulting current change through its inductor. This sets the positive terminal of the voltage follower 46 to ground until the computer 16 triggers the flip-flop 58 again.

The filament 34 can be reactivated to ionize subsequent component peaks in a number of ways. The pressure gauge 28, in gaseous communication with the ionization chamber 32, can provide feedback to the computer 16 indicating the solvent peak is passed. It is noted that, for example, a one-second delay involved in pressure detection by the pressure gauge is acceptable for reactivating the filament, although too slow for purposes of shutting off the filament. Alternatively, the computer 16 can reactivate the filament 34 after a predetermined time after the onset of the solvent peak.

The present invention can be applied in contexts other than GC/MS systems where it is desired to shut off a filament when the ambient pressure abruptly increases. The present invention provides for alternative methods of detecting changes in filament temperature, and for different ways detected changes can be used in shutting off the filament. For example, those skilled in the art can recognize a great variety of circuits equivalent to that described above. Other variations and modifications are provided for by the present invention, the scope of which is limited only by the following claims.

What is claimed is:

1. A system comprising:
    a filament for emitting electrons through thermal emission when sufficient current flows through said filament, said emitted electrons having sufficient energy to ionize molecules in an ambient gas characterizable by an ambient pressure;
    a power supply for supplying a current through said filament so that electrons are emitted therefrom, said power supply being electrically coupled to said filament, said current having an emission component corresponding to emitted electrons from said filament and a supply component corresponding to the portion of said current not accounted for by said emitted electrons;
    temperature means for sensing a drop in the temperature of said filament; and
    deactivation means for turning off the supply of power through said filament in response to a detection by said temperature means of a drop in temperature of said filament, said deactivation means being coupled to said temperature means and to said power supply;
    whereby, filament burnout due to contamination by ionized molecules is minimized since ionizing emissions are deactivated when said ambient pressure exceeds a threshold as detected by a drop in the temperature of said filament.

2. The system of claim 1 wherein said temperature means includes an emission current path for segregating said emission component through said filament from said supply component.

3. The system of claim 2 further comprising feedback means for regulating the magnitude of said emission current component by adjusting said power supply as a function of the magnitude of said emission current component.

4. The system of claim 1 further comprising pressure responsive means for reactivating said filament after said filament has been deactivated by said deactivation means when the pressure about said filament drops below at predetermined threshold.

5. The system of claim 1 further comprising timing means for reactivating said filament after said filament has been deactivated by said deactivation means after a predetermined time has elapsed.

6. A method of protecting an electron emitting filament from damage due to an increase in local pressure, said method comprising the steps of:
    emitting electrons from said filament by supplying a current therethrough so as to ionize molecules of ambient gas characterizable by an ambient pressure;
    monitoring said filament for the occurrence of a temperature drop therein; and
    shutting off a current through said filament when a temperature drop exceeding a predetermined criterion occurs at said filament;
    whereby, filament burnout due to contamination by ionized molecules is minimized since ionization is stopped when the number of molecules present as reflected in said ambient pressure increases to cause said temperature drop.

7. The method of claim 6 wherein said temperature drop is detected by detecting a drop in the emission current of said filament.

8. The method of claim 7 wherein said detecting a drop in emission current involves detecting a temperature-drop related perturbation in a feedback circuit regulating the current through said filament.

9. The method of claim 6 further comprising reactivating said current when the pressure about the filament drops below a predetermined threshold.

10. The method of claim 6 further comprising reactivating said current a predetermined time after said current is shut off in response to a temperature drop.

11. The system of claim 1 wherein said system is an ionization system for a mass spectrometer and further comprises an ionization chamber having a gas inlet for admitting gas therein so that said chamber can be characterized at any given time by a gas pressure, said filament being arranged with respect to said chamber so that said electrons are directed into said chamber and so that said gas pressure is said ambient pressure for said filament.

12. The system of claim 11 wherein said temperature means includes means for sensing a decrease in said supply component of said current through said filament.

13. The system of claim 1 wherein said temperature means includes means for sensing a decrease in said supply component of said current through said filament.

14. The method of claim 6 wherein said ambient gases are introduced through a gas inlet of a mass spectrometer ionization chamber arranged so that electrons emitted from said filament can ionize gas molecules contained therein.

15. The method of claim 14 wherein said step of monitoring involves detecting changes in a supply component of said current while maintaining a constant emission component of said current, said supply component corresponding to the portion of said current not accounted for by said emission component, said emission component being constituted by electrons emitted from said filament.

16. The method of claim 6 wherein said step of monitoring involves detecting changes in a supply component of said current while maintaining a constant emission component of said current, said supply component corresponding to the portion of said current not accounted for by said emission component, said emission component being constituted by electrons emitted from said filament.

* * * * *